United States Patent [19]

Colquhoun et al.

[11] Patent Number: 4,777,300
[45] Date of Patent: Oct. 11, 1988

[54] AROMATIC KETONE

[75] Inventors: Howard M. Colquhoun, Knutsford; James A. Daniels, Frodsham; David F. Lewis, Northwich, all of England

[73] Assignee: Imperial Chemical Industries PLC, London, England

[21] Appl. No.: 8,835

[22] Filed: Jan. 30, 1987

[30] Foreign Application Priority Data

Feb. 13, 1986 [GB] United Kingdom ............... 8603578

[51] Int. Cl.$^4$ .............................................. C07C 45/46
[52] U.S. Cl. ..................................... 568/319; 508/31; 508/306; 508/314
[58] Field of Search ................ 568/319, 322, 31, 306, 568/314

[56] References Cited

U.S. PATENT DOCUMENTS

| 3,073,866 | 1/1963 | Stanley ................... | 568/319 |
| 3,950,428 | 4/1976 | Feasey et al. .......... | 568/319 |
| 4,453,010 | 6/1984 | Staniland ............... | 568/319 |
| 4,604,485 | 8/1986 | Colquhoun ............ | 568/322 |
| 4,607,125 | 8/1986 | Mott ....................... | 568/319 |

FOREIGN PATENT DOCUMENTS

| 0075390 | 3/1983 | European Pat. Off. ............ | 568/319 |
| 0167286 | 1/1986 | European Pat. Off. ............ | 568/319 |
| 0199661 | 10/1986 | European Pat. Off. ............ | 568/319 |
| 2730991 | 1/1978 | Fed. Rep. of Germany ...... | 568/319 |
| 3402831 | 9/1984 | Fed. Rep. of Germany ...... | 568/319 |

OTHER PUBLICATIONS

Cullinani et al, J. Chem. Soc., pp. 2926–2929, (1958).

Primary Examiner—James H. Reamer
Attorney, Agent, or Firm—Cushman, Darby & Cushman

[57] ABSTRACT

An aromatic ketone having the formula XArCOPh-PhOH is made by contacting an ester of formula XAr-COOPhPh, where Ar is a divalent mono- or poly - aromatic group which may optionally be substituted;
Ph is para-phenylene; and
X is hydrogen or halogen or a nitro-, alkylsulphonyl-, arylsulphonyl-, alkylcarbonyl- or hydrocarbon group with a Friedel Crafts catalyst comprising one or more Lewis acids in an amount of at least 2.2 moles of such catalyst for each mole of the ester.

10 Claims, No Drawings

AROMATIC KETONE

The invention relates to aromatic ketones and the production thereof.

Hydroxy- or halo- substituted aromatic ketones can be used inter alia for the production of aromatic ketone polymers, particularly polyaryletherketones. In our pending British patent application No. 8601994 filed Jan. 28, 1986, we disclose a copolymer containing the repeating units —Ph—CO—Ph—Ph— joined to each other or to different repeating units by ether linkages, where Ph is para-phenylene. These repeating units can be obtained by the polycondensation of a substituted derivative of 4-benzoyl-4'-hydroxybiphenyl.

One possible technique for obtaining 4-benzoyl-4'-hydroxybiphenyl is by the rearrangement of 4-biphenylylbenzoate. The preparation of this compound by such a rearrangement is described by Fieser and Bradsher, J Am Chem Soc 58 (1936) pages 2337 and 2338, who report a yield of only 22%. Furthermore, Fieser and Bradsher make reference to apparently conflicting results obtained by Blicke and Weinkauff, J Am Chem Soc 54 (1932) pages 330 to 334 and by Hey and Jackson, J Chem Soc (1936) pages 802 to 806. Fieser and Bradsher report difficulty in achieving the results of Blicke and Weinkauff and state a belief that the conditions of Blicke and Weinkauff "are not very satisfactory". Hey and Jackson, using similar conditions to those of Blicke and Weinkauff, had been able to isolate only 3-benzoyl-4-hydroxybiphenyl.

4-biphenylylbenzoate can be obtained by esterification of a benzoylhalide with 4-hydroxybiphenyl and hence is potentially a satisfactory starting material for the production of 4-benzoyl-4'-hydroxybiphenyl. However, the attractiveness of such a procedure is reduced by the low yield, indeed the apparent difficulty in obtaining any, of the desired product.

We have now found that, by a modification of the procedure of Fieser and Bradsher, an improved yield of the desired product can be obtained.

The invention provides a process for the production of an aroyl or a heteroaroyl hydroxybiphenyl having the formula XArCOPhPhOH which comprises contacting a biphenyl arylate ester or heteroarylate ester of the formula XArCOOPhPhH where Ar is a divalent mono - or poly - aromatic group which may optionally be substituted;
Ph is para-phenylene; and
X is hydrogen or halogen or a nitro-, alkylsulphonyl-, arylsulphonyl-, alkylcarbonyl-, arylcarbonyl- or hydrocarbon group with a Friedel Crafts catalyst in an amount of at least 2.2 moles of such catalyst for each mole of the ester, such catalyst comprising one or more Lewis acids.

Ar may be a heterocyclic group such as pyridyl but is preferably a hydrocarbon group such as phenylene, biphenylene or naphthylene. The process is conveniently used for the production of 4-benzoyl-4'-hydroxybiphenyl or substituted derivatives thereof, in which Ar is para-phenylene.

Ar may carry one or more substituent groups in addition to, and the same as or different from, X.

If X is a hydrocarbon group, it may be for example alkyl, aryl, aralkyl, alkaryl or cycloalkyl. It preferably contains 1 to 15 carbon atoms and especially is alkyl containing 1 to 6 carbon atoms. If the hydroxybiphenyl derivative is to be used for the production of an aromatic ketone polymer, X is preferably halogen, especially chlorine or fluorine.

The specified proportion of Friedel Crafts catalyst results in an increased yield of the desired 4-aroyl or heteroaroyl-4'-hydroxybiphenyl compound, for example 60% or more by weight, relative to the arylate or heteroarylate ester starting material. The amount of catalyst is preferably at least 2.5, especially at least 3.0, for example about 3.4, moles for each mole of ester. We obtained satisfactory yields (in excess of 60% by weight) using at least 3.0 moles, for example about 3.4 moles, of aluminium chloride (as the Friedel Crafts catalyst) for each mole of ester. The preferred proportion of catalyst will depend on the material used as catalyst and on the nature of the ester.

As Friedel Crafts catalysts which may be used there may be mentioned Bronsted acids such as hydrogen fluoride and trifluoromethanesulphonic acid, and Lewis acids such as boron trifluoride, aluxinium chloride, aluminium brotide, zinc chloride and ferric chloride. Possibly a mixture of such acids may be used. Preferably the catalyst is Lewis acid to the extent of at least 80% molar, especially 100%. It is convenient to use aluminium chloride since it is relatively inexpensive and gives few hazards.

The temperature and time of contacting is dependent on the nature of the ester and the Friedel Crafts catalyst. Contacting is preferably effected in a liquid which is a solvent for the ester under the conditions.

Suitable liquids include 1,2-dichlorobenzene, nitrobenzene, 1,2,4-trichlorobenzene and 1,1,2,2-tetrachloroethane. Using aluminium chloride as catalyst, the reaction is preferably effected at at least 60° C., particularly at least 100° C., for example at 120° C. The time of contacting is dependent on the temperature and will be less at higher texperatures. The time of contacting is typically at least one hour and may be from 4 to 20 hours, for example 6 to 10 hours.

At the end of contacting, the reaction mixture contains the desired aroyl or heteroaroyl hydroxybiphenyl together with undesired by-products such as the 4, 3 isomer. Conveniently the desired aroyl or heteroaroyl hydroxybiphenyl isomer is precipitated from the reaction mixture by the addition of an acidic aqueous solution, for example by adding a mixture of aqueous hydrochloric acid and methanol. The recovered solid is then preferably washed with a neutral solution, for example a mixture of water and methanol, to remove most of the acid used to precipitate the solid. The solid may finally be washed with a relatively volatile liquid to remove unwanted by-products and reaction solvent, and dried, for example by heating under reduced pressure. The solid may be purified by recrystallisation from a suitable solvent mixture, for example an isopropyl alcohol - ethyl acetate mixture subsequent to treatment of the solution with a decolorising solid such as carbon black.

The solid obtained may be used for the preparation of an aromatic ether ketone copolymer as described in our aforementioned British Patent Application.

The process of the invention occurs by the Fries rearrangement of an ester to form a hydroxyketone. The ester may be preformed but is conveniently formed in situ, for example by the reaction of a suitable acid, acid halide or acid anhydride with a corresponding phenolic compound. Most preferably, benzoic acid or the corresponding acid halide or anhydride is reacted with hydroxybiphenyl and, on completion of this reaction, the reaction mixture containing the ester is contacted with the Friedel Crafts catalyst.

Thus, in a further aspect the invention provides a process for the production of an aroyl or heteroaroyl hydroxybiphenyl of formula XArCOPhPhOH which comprises reacting a compound of formula XArCOY with a compound of formula HOPhPhH and thereafter contacting the reaction mixture with at least 2.2 moles of Friedel Crafts catalyst for each mole of the compound XArCOOPhPhH, formed or formable by such reacting, where
Ar, Ph and X are all as defined; and
Y is halogen, OH or - OOCPhX, said Friedel Crafts catalyst comprising at least one Lewis acid.

Y is preferably halogen especially chlorine. The first reaction, esterification, is typically effected in a solvent for the reactants and product, particularly using a liquid as specified above for the contacting with the Friedel Crafts catalyst, for example 1,2-dichlorobenzene. The esterification reaction can be effected in the presence of a small proportion of a mineral acid to catalyse it. The reaction time and temperature are preferably such that essentially complete reaction occurs to give the ester, for example, a temperature of at least 80° C., particularly at least 100° C. and a time of at least one hour, particularly 4 to 16 hours.

If a benzoyl halide is used, the hydrogen halide formed is conveniently evolved and removed from the reaction mixture, ths evolution of hydrogen halide being monitored to follow the course of the reaction. When the reaction has been completed, the excess of the Friedel Crafts catalyst may be added to the reaction mixture, whilst maintaining the elevated reaction temperature, to effect the subsequent stage of the process. However, whilst the foregoing procedure is preferred for commercial operation, it will be appreciated that there may be an interval between the two stagas.

Further aspects of the invention are set out in the following illustrative examples.

EXAMPLE 1

Synthesis of 4-(4-chlorobenzoyl)-4'-hydroxybiphenyl 330.0 g (248 cm$^3$, 1.885 mole) of 4-chlorobenzoyl-chloride, 321.0 g (1.885 mole) of 4-hydroxybiphenyl, 1 cm$^3$ of concentrated sulphuric acid and 2.5 dm$^3$ of 1,2-dichlorobenzene were stirred together at 120° C. in a 5 dm$^3$ 3-necked flask fitted with a nitrogen inlet, reflux condenser and stirrer. Evolution of hydrogen chloride was monitored until it ceased after about 6–7 hours. After a further 2 hours at 120° C. the flask and contents were allowed to cool overnight with stirring.

865.0 g (6.29 mole) of powdered anhydrous aluminium chloride were added to the stirred flask at 20°–30° C. over a 15 minute period. The flask and contents were heated to 120°–130° C. and held at that temperature for 7 to 8 hours, then allowed to cool to 20° C. overnight, with stirring.

The contents of the flask were then evenly syphoned (with applied nitrogen pressure) into 5 beakers each of 5 dm$^3$ capacity, each containing a stirred solution of 2.5 dm$^3$ of normal aqueous hydrochloric acid and 0.5 dm$^3$ of methanol. The contents of the beakers were stirred for about 15 minutes then the off-white solid was allowed to settle. The acid layer above the solid was syphoned off and a solution of 2 dm$^3$ of water and 0.35 dm$^3$ of methanol was added to the stirred contents of the beaker. After about 15 minutes the solid was again allowed to settle. Treatment of the solid with water and methanol was repeated until the solution above the solid was neutral (pH at least 7).

The neutral aqueous layer was syphoned off and a solution of 1.5 dm$^3$ of toluene and 0.25 dm$^3$ of methanol was added to each beaker. The contents of the beakers were then filtered through a buchner funnel with water vacuum. The solid on the filter was washed toluene to remove dichlorobenzene and unwanted isomers, then dried in a vacuum oven at 130° C. and 40 kN/m$^2$ pressure for 16 hours.

The crude solid was recrystallised from a refluxing mixture of isopropyl alcohol and ethyl acetate (4:1 by volume) with decolorising carbon black present, with filtration of the mixture whilst hot through a bed of Celite (kieselguhr) on a hot glass buchner funnel (sinter No2). The crystallised product was obtained in a 67% yield and had a melting point of 197°–198.5° C. By analysis the product was found to contain 73.6% by weight of carbon (calculated 73.9%) and 4.3% by weight of hydrogen (calculated 4.3%). Proton and carbon -13 nmr and the infra-red spectrum, confirmed the structure as that of 4-(4-chlorobenzoyl)-4'-hydroxybiphenyl.

COMPARATIVE EXAMPLE A 42.5g of 4-hydroxybiphenyl and 44.0g (32 cm$^3$) of 4-chlorobenzoylchloride were added to 500 cm$^3$ of 1,2-dichlorobenzene in a one dm$^3$ 3-necked flask fitted with a stirrer, reflux condenser and a nitrogen inlet. One cm$^3$ of concentrated sulphuric acid was added as catalyst.

The stirred solution was heated to 110°–120° C. and held at that temperature for 7 hours. The solution became a clear pale brown colour after 30 minutes. Hydrogen chloride was evolved especially heavily during the first 3 hours of reaction but little or no hydrogen chloride was detected after 6 hours.

The flask was cooled overnight then 70g of aluminium chloride were added with stirring (mole ratio of aluminium chloride 4-hydroxybiphenyl 2.1:1).

The mixture was heated to 120°–130° C. and maintained at that temperature for six hours. The solution was allowed to cool and poured into 3 dm$^3$ of a solution containing 2.5 dm$^3$ of normal hydrochloric acid and 0.5 dm$^3$ of methanol. The precipitate was pale-yellow in colour indicating the presence of some ortho isomer (3-(4-chlorobenzoyl)-4-hydroxybiphenyl).

The stirring was stopped, the precipitate allowed to settle then the aqueous layer was removed. A solution of 2 dm$^3$ of water and 0.5 dm$^3$ of methanol was added and the solution stirred again. After about 15 minutes the solid was again allowed to settle and the liquid was syphoned off. This treatment was repeated until a neutral solution was obtained. After removal of the final water/methanol mixture, the precipitate was filtered off and washed with toluene to remove the ortho isomer. The remaining grey solid was recrystallised from 1,2-dichloroethane to give silvery-grey crystals of melting point 197°–198° C. in a 27% yield.

EXAMPLE 2

The procedure of Example 1 was repeated with the following exceptions. 192g of 4-hydroxybiphenyl (1.13 moles) and 179g of 4-fluorobenzoyl chloride (1.13 moles) were heated in 1.5 dm$^3$ of 1,2 -dichlorobenzene wdth 0.5 cm$^3$ of concentrated sulphuric acid. After cooling to ambient temperature, 519g of aluminium chloride (3.89 moles) were added with stirring. The temperature was raised to 120° C. with mechanical stirring, and the reaction mixture was stirred at this temperature for a further 8 hours. After cooling to ambient temperature, the dark solution formed was poured, with stirring, into three beakers each of 5 dm$^3$ and each containing 2 dm$^3$ of normal aqueous hydrochloric acid and 0.5 dm$^3$ of methanol. Extractions of the organic phase until aqueous extracts were neutral were carried out as in Example 1. The crude solid product was isolated by filtration of the organic phase and washing the filter cake successively with water, toluene, and 40°–60° petroleum ether. After drying at 130° C. under vacuum (40 kN/m$^2$) for 16 hours, this material was recrystallised from mixed xylene isomers ( 2.7 dm$^3$) in the presence of carbon black, with filtration through kieselguhr while hot, to give 207g (63% yield) of a cream, crystalline product, mp 190°–191° C., whose proton and carbon -13 nmr, infra-red and mas spectra were all in agreement with the structure being that of 4-(4-fluorobenzoyl)-4'-hydroxybiphenyl.

COMPARATIVE EXAMPLE

This procedure was similar to that of Comparative Example A with the following exceptions. 53.7g of 4-hydroxybiphenyl (0.32 moles) and 50g of 4-fluorobenzoyl chloridc (0.32 moles) were heated in 0.42 dm$^3$ of 1,2-dichlorobenzene, with 0.14 cm$^3$ of concentrated sulphuric acid, to 120° C. for 8 hours. The mixture was cooled to room temperature and 42 g anhydrous aluminium chloride (0.32 moles) were added. The temperature was raised to 120° C. and the mixture was stirred at this temperature for 8 hours. Work-up and purification of the product as described in Example 2 yielded only 3.Og of a white crystalline material identified by infra-red and proton nmr spactra and melting point (162° C.) as 4-biphenylyl-4-fluorobenzoate, the ester formed as an intermediate product, in situ, during the first stage of the reaction. 4-(4-fluorobenzoyl)-4'-hydroxybiphenyl was not detected as a product of this procedure. The intense yellow colour of the organic phase, after the final reaction mixture had been quenced into the aqueous hydrochloric acid/methanol mixture, strongly suggested that considerable amounts of 3-(4-fluorobenzoyl)-4-hydroxybiphenyl (yellow) had been formed, that is some rearrangement to the orthoproduct had occurred.

The examples and comparative examples illustrate ths effect of varying the molar ratio of aluminium chloride to 4-hydroxybiphenyl, the molar ratios being Example 1—3.34:1

Comparative Example A—2.1:1

Example—2, 3.44:1

Comparative Example B—1:1

At high proportions of the Friedel Crafts catalyst (aluminium chloride), the desired 4,4'-isomer is obtained in a yield of more than 60% whereas, at low proportions thereof, the yield of the 4,4'-isomer is low or is even undetectable.

We claim:

1. A process for the production of an aroyl hydroxybiphenyl having the formula

XArCOPhPhOH which comprises contacting a biphenyl arylate ester of the formula

XArCOOPhPhH where

Ar is a phenylene, biphenylene or naphthylene group;

Ph is para-phenylene; and

X is hydrogen or halogen or a nitro-, alkylsulphonyl-, arylsulfonyl-, alkylcarbonyl-, arylcarbonyl- or hydrocarbon group with a Friedel Crafts catalyst in an amount of at least 2.2 moles of such catalyst for each mole of the ester, such catalyst consisting essentially of a Lewis acid selected from the group consisting of $BF_3$, $AlCl_3$, $AlBr_3$, $ZnCl_2$, $FeCl_3$, and mixtures thereof , wherein said process is effected in the presence of a liquid which is a solvent for the ester.

2. A process as claimed in claim 1 in which at least 2.5 moles of Friedel Crafts catalyst are used for each mole of the ester.

3. A process as claimed in claim 2 in which at least 3 moles of Friedel Crafts catalyst are used.

4. A process as claimed in claim 1 in which the Friedel Crafts catalyst is aluminium chloride.

5. A process as claimed in claim 1 which is effected at a temperature of at least 100° C.

6. A process as claimed in claim 1 in which the compound of formula

XArCOPhPhOH is precipitated from the reaction mixture by the addition to the reaction mixture of an acidic solution.

7. A process as claimed in claim 1 in which the ester is formed in situ by the reaction of an acid, acid halide or acid anhydride with a phenolic compound.

8. A process as claimed in claim 7 which uses an acid halide as starting material and is effected in a liquid which is a solvent for the reactants and reaction products and the same liquid is used for the subsequent contacting of the ester with Friedel Crafts catalyst.

9. A process according to claim 1 wherein X is hydrogen or halogen, Ar is phenylene, the Friedel Crafts catalyst is aluminum chloride, the amount of catalyst is at least 3.0 moles for each mole of ester, the temperature is at least 100° C. and the yield is at least 60% by weight based on the weight of ester starting material.

10. The process of claim 1 wherein the solvent is selected from the group consisting of 1,2-dichlorobenzene, nitrobenzene, 1,2,4-trichlorobenzene and 1,1,2,2-tetrachloroethane.

* * * * *